(12) United States Patent
Farber et al.

(10) Patent No.: US 11,446,338 B2
(45) Date of Patent: Sep. 20, 2022

(54) FOOD, COSMETIC AND PHARMACEUTICAL FORMULATION WITH AN IMMUNOMODULATORY AND PROTECTIVE ANTI-VIRAL EFFECT

(71) Applicants: Boris Farber, Brooklyn, NY (US); Sof'ya Farber, Brooklyn, NY (US)

(72) Inventors: Boris Farber, Brooklyn, NY (US); Sof'ya Farber, Brooklyn, NY (US); Artur Viktorovich Martynov, Kharkov (UA)

( * ) Notice: Subject to any disclaimer, the term of this patent is extended or adjusted under 35 U.S.C. 154(b) by 0 days.

(21) Appl. No.: 16/954,854

(22) PCT Filed: May 4, 2018

(86) PCT No.: PCT/RU2018/000292
§ 371 (c)(1),
(2) Date: Jun. 17, 2020

(87) PCT Pub. No.: WO2019/212379
PCT Pub. Date: Nov. 7, 2019

(65) Prior Publication Data
US 2021/0085729 A1     Mar. 25, 2021

(51) Int. Cl.
| | |
|---|---|
| A61K 35/742 | (2015.01) |
| A61K 45/06 | (2006.01) |
| A61K 31/196 | (2006.01) |
| A61K 31/205 | (2006.01) |
| A61K 36/064 | (2006.01) |
| A61K 36/484 | (2006.01) |
| A61K 36/28 | (2006.01) |
| A61K 35/748 | (2015.01) |
| A61K 36/48 | (2006.01) |
| A61K 31/714 | (2006.01) |
| A61K 31/525 | (2006.01) |
| A61K 31/51 | (2006.01) |
| A61K 31/519 | (2006.01) |
| A61K 31/7048 | (2006.01) |
| A61K 31/198 | (2006.01) |
| A61K 31/145 | (2006.01) |
| A61K 36/66 | (2006.01) |
| A61K 31/472 | (2006.01) |
| A61K 8/99 | (2017.01) |
| A61K 8/44 | (2006.01) |
| A61K 8/9789 | (2017.01) |
| A61K 8/9728 | (2017.01) |
| A61K 8/67 | (2006.01) |
| A61K 8/60 | (2006.01) |
| A61K 8/46 | (2006.01) |
| A61K 8/49 | (2006.01) |
| A61Q 11/00 | (2006.01) |

(Continued)

(52) U.S. Cl.
CPC .......... *A61K 35/742* (2013.01); *A23L 33/105* (2016.08); *A23L 33/135* (2016.08); *A23L 33/15* (2016.08); *A23L 33/175* (2016.08); *A23L 33/40* (2016.08); *A61K 8/44* (2013.01); *A61K 8/445* (2013.01); *A61K 8/466* (2013.01); *A61K 8/4926* (2013.01); *A61K 8/602* (2013.01); *A61K 8/673* (2013.01); *A61K 8/9728* (2017.08); *A61K 8/9789* (2017.08); *A61K 8/99* (2013.01); *A61K 31/145* (2013.01); *A61K 31/196* (2013.01); *A61K 31/198* (2013.01); *A61K 31/205* (2013.01); *A61K 31/472* (2013.01); *A61K 31/51* (2013.01); *A61K 31/519* (2013.01); *A61K 31/525* (2013.01); *A61K 31/7048* (2013.01); *A61K 31/714* (2013.01); *A61K 35/748* (2013.01); *A61K 36/064* (2013.01); *A61K 36/28* (2013.01); *A61K 36/48* (2013.01); *A61K 36/484* (2013.01); *A61K 36/66* (2013.01); *A61K 45/06* (2013.01); *A61Q 11/00* (2013.01); *A23V 2002/00* (2013.01)

(58) Field of Classification Search
CPC .......................... A61K 35/742; A61L 33/135
See application file for complete search history.

(56) References Cited

U.S. PATENT DOCUMENTS 5,455,033 A * 10/1995 Silverman ............ A61K 36/886
424/737
5,580,857 A * 12/1996 Oden .................... A61K 31/70
514/25

(Continued)

FOREIGN PATENT DOCUMENTS

CN          101543629 A  *  9/2009

OTHER PUBLICATIONS

Seki, H., K. Tamura and T. Muranaka. Plant-derived isoprenoid sweeteners: recent progress Bioscience, Biotechnology, and Biochemistry, 2018 vol. 82, No. 6, 927-934. (Year: 2018).*
Cambridge online Dictionary, definition of "vitamin" (Year: 2021).*
Merriam-Webster's Online Dictionary defines "derivative" (Year: 2018).*

(Continued)

*Primary Examiner* — Michael P Cohen
(74) *Attorney, Agent, or Firm* — Daniel M. Cohn; Howard M. Cohn

(57) ABSTRACT

Field of application: the invention relates to biotechnology, can be used in the food industry, medicine and cosmetology in the prevention and/or treatment of diseases associated with immunodeficiencies and respiratory viral infections.
The proposed food, cosmetic and pharmaceutical composition with an immunomodulating and protective antiviral effect additionally has the ability to completely prevent infection by a number of viruses, including influenza, rotavirus and coronavirus, as well as stimulate the immune system more than individual probiotics.

24 Claims, No Drawings

(51) Int. Cl.
*A23L 33/135* (2016.01)
*A23L 33/105* (2016.01)
*A23L 33/175* (2016.01)
*A23L 33/15* (2016.01)
*A23L 33/00* (2016.01)

(56) References Cited

U.S. PATENT DOCUMENTS

| | | | | |
|---|---|---|---|---|
| 6,521,239 | B1* | 2/2003 | Breton | A61Q 19/00 424/401 |
| 8,795,724 | B2* | 8/2014 | Caillard | A61P 7/02 424/464 |
| 2003/0003107 | A1* | 1/2003 | Farmer | A61K 8/925 424/184.1 |
| 2004/0013618 | A1* | 1/2004 | Passi | A61K 8/365 424/59 |
| 2005/0032674 | A1* | 2/2005 | Kelly | A61K 36/06 424/780 |
| 2006/0263344 | A1 | 11/2006 | Skop et al. | |
| 2013/0251695 | A1 | 9/2013 | Farmer et al. | |

OTHER PUBLICATIONS

Machine translation of CN 101543629(A), provided by EPO (Year: 2021).*

V.K. Gupta, S. Malhotra. Pharmacological attribute of Aloe vera: Revalidation through experimental and clinical studies. AYU, Apr.-Jun. 2012, vol. 33, Issue 2, 193-196. (Year: 2012).*

E. Del Duca, et al. Superiority of a vitamin B12-containing emollient compared to a standard emollient in the maintenance treatment of mild-to-moderate plaque psoriasis (International Journal of Immunopathology and Pharmacology 30(4), 2017, 439-444. (Year: 2017).*

Z. Degim, et a. An investigation on skin wound healing in mice with a taurine-chitosan gel formulation. Amino Acids (2002) 22: 187-198 (Year: 2002).*

Google patent search—Jan. 15, 2021_succinylation of bacillus coagulans (Year: 2021).*

Google patent search—Apr. 14, 2021_topical papaverine-erectile (Year: 2021).*

Google scholar search_Apr. 14, 2021_papaverine anti-inflammatory (Year: 2021).*

W. Abhyankar, L. J. de Koning, S. Brul & C. G. de Koster. Spore proteomics: the past, present and the future. FEMS Microbiol Lett 358 (2014) 137-144. (Year: 2014).*

D.F. Ohye and W.G. Murell. Formation and Structure of the Spore of Bacillus Coagulans. J. Cell Biol. 14, 1962, 111-123. (Year: 1962).*

M. Alleyn, M. Breitzig, R. Lockey, and N. Kolliputi. "The dawn of succinylation: a posttranslational modification," Am J Physiol Cell Physiol 314: C228-C232, 2018. First published Nov. 22, 2017 (Year: 2017).*

D. F. Ohye and W. G. M Urrell. Formation and Structure of the Spore of Bacillus Coagulans. J. Cell Biol, vol. 14, 1965, p. 121 (Year: 1965).*

* cited by examiner

FOOD, COSMETIC AND PHARMACEUTICAL FORMULATION WITH AN IMMUNOMODULATORY AND PROTECTIVE ANTI-VIRAL EFFECT

The invention relates to biotechnology. The invention can be used in the food industry, medicine and cosmetology. Specifically, in the prevention and/or treatment of diseases associated with immunodeficiencies and respiratory viral infections.

The main application of probiotics is in treating or preventing diseases of the gastrointestinal tract. These microorganisms have antagonistic activity against pathogenic and conditionally pathogenic intestinal bacteria, ensuring the restoration of normal intestinal microflora. At the same time the probiotics promote the digestion of food components, produce substances necessary for the body (carboxylic acids, vitamins), and stimulate local immunity. In addition, they can be used in the treatment of other diseases, including, gynecological, allergic, and cardiovascular.

In order for a Microorganisms to be classified as belonging to probiotics they must have:
- Resistance to hydrochloric acid and bile, this allows them to survive when passing through the upper sections of the digestive system
- Ability to adhere to the epithelial cells of the intestinal mucosa;
- The ability to multiply rapidly by colonizing in the intestines;
- The ability to normalize the composition of intestinal microflora;
- The ability to persist in the intestine even after the manifestation of its effects;
- To have no signs of pathogenicity
- Remain viable in pharmaceutical preparations, i.e. possess resistance to technological processes in the production of drugs and to storage at room temperature.

To a greatest extent, these requirements correspond to microorganisms capable of forming spores.

The effectiveness of spore-forming bacteria has been proven in clinical studies. Due to the high resistance of these bacteria, it manifests itself even more than the traditional, non-spore forming probiotics. It is indicated that representatives of such groups of spore-forming bacteria as *Bacillus, Brevibacillus, Clostridium, Sporolactobacillus* suppress intestinal disorders more efficiently than classical probiotics based on lactobacilli and bifidobacteria. At the same time, debates continue over whether spores or vegetative forms are responsible for probiotic activity.

One of the most promising spore-forming microorganisms is the spore-forming lactobacillus *Bacillus coagulans*. In the form of spores, it tolerates technological processes and storage well, it does not collapse under the influence of gastric juice and bile. Once it is in the duodenum, spores of *Bacillus coagulans* can germinate in vegetative bacteria in the lumen of the human intestine and exert their probiotic effects. *Bacillus coagulans* is not only a part of dietary supplements, *Bacillus coagulans* recently became part of the drugs with proven clinical efficacy as it appeared on the global pharmaceutical market.

This bacterium is presented in the American Cell Culture Collection (ATCC, Rockville, Md.): *Bacillus coagulans* Hammer NRS 727 (ATCC No. 1 1014), *Bacillus coagulans* Hammer strain C (ATCC No. 11369); *Bacillus coagulans* Hammer (ATCC No. 31284), *Bacillus coagulans* Hammer NCA 4259 (ATCC No. 15949), *Bacillus coagulans* strain ATCC 7050. Purified bacteria *Bacillus coagulans* are also available in the Deutsche Sarumlung von Mikroorganismen und Zellkuns Braell collections, Germany: *Bacillus coagulans* Hammer 1915 (DSM No. 2356), *Bacillus coagulans* Hammer 1915 (DSM No. 2383, consistent with ATCC No. 1 1014), *Bacillus coagulans* Hammer (DSM No. 2384, consistent with ATCC No. 11369), and *Bacillus coagulans* Hammer (DSM No 2385, consistent with ATCC No. 15949). *Bacillus coagulans* is also produced commercially by manufacturers such as Sabinsa Corporation (Piscataway, N.J.) or K K Fermentation (Kyoto, Japan).

The spore of *B. coagulans* is located at one of the poles of the cell and has the shape of an ellipse. Additionally itis resistant to heat and other adverse environmental conditions and can grow from dilute solutions of hydrochloric acid and sodium hydroxide. It forms colonies of about 2.5 mm in diameter, which have a convex shape, are shiny, and do not emit any pigments.

By biological properties, it occupies an intermediate position between two genera—*Bacillus* and *Lactobacillus*. Being a spore-forming bacterium, it simultaneously produces lactic acid, is not capable of reducing nitrates, and does not contain oxidase.

A number of properties combine *Bacillus coagulans* with members of the genus. *Bacillus* first of all has the ability to form spores and colonies. The microorganism uses substances like carbohydrates, peptones, meat and yeast extract for its growth. It produces acids from substrates such as arabinose, xylose, glucose, galactose, mannose, fructose, maltose, sucrose and trehalose. The *Bacillus coagulans* does not hydrolyze starch, casein, gelatin, it does not produce hydrogen sulfide and indole.

However, there are characteristics that distinguish *Bacillus coagulans* from the genus of *Bacillus*. The bacterium *Bacillus coagulans* has a predominantly curved shape, and lactic acid bacteria, which are curved shape as well. Like *Bacillus coagulans*, lactic acid bacteria exhibit very low motility. In *Bacillus coagulans* and in lactic acid bacteria, spores are located in the terminal portion of the cell, and not in the center, as they are in *Bacillus*.

And they usually negative on the oxidase test. This will form dextrorotatory lactic acid from glucose, fructose, sucrose and trehalose. Unlike most *Bacillus*, it does not restore nitrates to nitrites. In *Bacillus* DNA, the molar percentage of the guanine-cytosine pair reaches 69%, while in *Lactobacillus* it does not exceed 53%.

At the same time, *Bacillus coagulans* spores are resistant to antibiotics. Due to this fact, the probiotic can be used together, along with standard chemotherapy, without the risk of suppressing its activity.

In the gastrointestinal tract, there are protective mechanisms that prevent excessive reproduction and prevent the introduction of unusual, none characteristic microflora. These mechanisms include: acidic contents of the stomach, bile acids, epithelial integrity, brush border and immune defense.

The main bactericidal effect in the human gastrointestinal tract is carried out by three factors—gastric secretion, hydrochloric acid and bile. The acidic environment of the stomach (pH 3) and proteases (pepsin) destroy most of the bacteria that enter through food. Experimental and clinical studies have shown that under the influence of gastric juice and bile, probiotics lose up to 90% of their activity before they enter the intestine.

According to in vitro experiments, *Bacillus coagulans* in the vegetative form cannot withstand in a medium with $pH \leq 3$. However it was shown that the *Bacillus coagulans* CNCMI-1061 strain, used as a probiotic in chickens, retains up to 50% of its living strains in the acidic environment of the human stomach. However, in the form of spores, all bacteria of the genus *Bacillus*, including *Bacillus coagulans*, are resistant to acidic pH values.

For *Bacillus coagulans* spores, acid activation has not been discovered. It is noted that spores pass the stomach and germinate only in the duodenum.

Therefore, *Bacillus coagulans* formed in the spores would ensure its resistance to the acidic contents of the stomach. It is noted that when it enters the stomach, the spores of this microorganism can withstand a long stay in the acidic environment of the stomach and are not destroyed or digested by gastric juice.

Bile serves as a second barrier for microorganisms, because it contains salts of bile acids which are toxic to microorganisms and salts of bile acids. These make up about 50% of bile composition. Resistance to the action of bile acids is one of the main criteria for the selection of microorganisms for use as probiotics.

A bile concentration of 0.3% is critical and is used to test the sensitivity of various probiotic microorganisms to it.

Other negative effects of bile acids are disturbances in DNA structure due to suppression of its repair processes, oxidative stress, decrease in intracellular pH, decrease in intracellular levels of calcium and iron (due to their chelation).

It is was shown that *Bacillus coagulans*, even not in spore form, have a fairly high resistance to the action of bile acids.

If *Bacillus coagulans* is sufficiently resistant to the action of the first two factors (acid and bile), then the occurrence of anaerobic conditions (despite the fact that it is not an obligate anaerobic) or, possibly, ther unfavorable factors, lead to the fact that this microorganism in the distant intestine *Bacillus coagulans* undergoes resporulation, and largely in this sporulation form it leaves the human body.

Clinical experience of using probiotics based on *Bacillus coagulans* indicates that they are safe. Their pharmacological activity is determined only by local action in the intestinal lumen and by immunological mechanisms. The activity is mediated by the entry of bacteria or their spores into the lymphatic system.

Important aspects in the action of probiotics based on spores of microorganisms is the germination of spores and the formation of vegetative forms. The relative number of vegetative forms, the degree of proliferation, and the question is which forms probiotics exhibit biological activity—spores, vegetative microorganisms or their elements (metabolites and cell walls).

We present already published data on the kinetics of *Bacillus coagulans* in the human intestine. Data in the literature indicate that, on average, the time between taking *Bacillus coagulans* and spore germination is 4 hours. Peak accumulation of bacterial mass is observed after 18 hours.

*Bacillus coagulans* are excreted slowly from the body—after the last probiotic intake, spores in the feces are detected within 7 days. This phenomenon is considered as a great clinical advantage. After the last dose of the drug its action lasts for an entire week, which allows quickly and fully, without the risk of complications and relapses, restores the function of the gastrointestinal tract after a disease.

The great importance of the *Bacillus coagulans*, lies in the fact that it is finally eliminates from the human body—this helps to restore our own microflora, which is native to humans, without the risk of introducing genetically foreign strains into it Therefore, *Bacillus coagulans* belongs to semi-residential lactobacilli—after it performed the function of probiotic in the human body, it leaves the body. This is also considered as an advantage of this particular microorganism, as it helps to restore its own microflora. Microflora are unique and individual for each person, without the risk of introducing genetically foreign strains into it.

*Bacillus coagulans* have advantages over most other bacteria, which have been used as probiotics. It occupies an intermediate position between the genera *Bacillus* and *Lactobacillus*, being a spore-forming bacterium producing lactic acid.

This bacterium in the form of spores well tolerates to effects of various technological processes, it resistant to antibiotics and does not disabled under the influence of gastric juice and bile. Once *Bacillus coagulans* are in the duodenum, the spores mature and begin to multiply, providing probiotic effects.

*Bacillus coagulans* belong to semi-resident bacteria—having performed the function of a probiotic in the human body, it goes through the sporulation phase and slowly leaves the body, excreting itself with feces in the form of spores. Therefore, it does not violate the individual composition of the intestinal mycoflora.

*Bacillus coagulans* improve the microbiological composition of the intestine, increasing the number of obligate microorganisms and displacing the pathogenic flora. During an experimental study on laboratory animals with experimental bacterial dysbiosis *Bacillus coagulans* were able to suppress the growth of pathogenic microorganisms and the resumption of functioning was observed. These results were due to the restoration of enzyme formation, as well as the normalization of the number of microbial cells of the normal intestinal microflora. The acute intestinal pathologies artificially caused in animals by pathogenic microorganisms were also quickly eliminated by using *Bacillus coagulans*.

The study on mice with vancomycin-resistant enterococci showed that the use of *Bacillus coagulans* lead to a statistically significant decrease in the number of these enterococci compared with untreated mice. In this experiment, bacteria was injected at a dose of 107 CFU per animal (or saline in the control) once a day for 4 days. In the experimental group, the number of vancomycin-resistant enterococci after therapy with *Bacillus coagulans* decreased by 35% against 0% in the control group (P=0.03). Experience has shown the effectiveness of *Bacillus coagulans* for the suppression of colonization of the intestine by multiresistant bacteria, and in the long term as a means of treating multiresistant colitis.

With respect to pathogenic microflora, probiotics in general can have the following effects:

1. Direct antagonistic, inhibitory effect on certain groups of microorganisms. The mechanism of action—the production of substances with antibacterial action; competition for food substrates; competition for binding sites.

2. Change in the metabolism of microorganisms—increase or suppression of enzymatic activities.

3. Stimulation of immunity—by increasing levels of antibodies, macrophage activity.

Let's evaluate which of these mechanisms of action are characteristic of *Bacillus coagulans* and which are perhaps the most important in the implementation of its probiotic effects.

It is believed that the inhibitory activity of *Bacillus coagulans* against putrefactive bacteria is partially determined by the secretion of bacteriocins. *Bacillus coagulans* produce coagulin—a bacteriocin belonging to the pediocin family. It is a peptide consisting of 44 amino acid residues, the sequence of which is similar to that of pediocins.

Coagulin and pediocin differ only in one amino acid found in the C-terminal region. Its molecular weight is in the range of 3-4 kDa. This bacteriocin is encoded by an approximately 14 kB fragment in plasmid pI4.

The latter expresses this bacteriocin rather stabely and independently. The inhibitory effect of coagulin has been established against intestinal bacteria of the genera *Enterococcus, Leuconostoc, Oenococcus, Listeria* and *Pediococcus* has been established. At the same time the probiotic can exhibit both bacteriostatic and bactericidal effects. Coagulin is stable at temperatures up to 60° C., has a pH in the range of 4-8, and does not break down under the influence of α-amylase, lipase or organic solvents. Coagulin is a peptide and is inactivated by proteases.

Another well-studied bacteriocin from this microorganism is lactosporin. It is secreted by the bacterium in a small concentration and only in the presence of a pathogenic target bacteria in the nutrient medium or the intestine. The antimicrobial activity of lactosporin was also confirmed against the target—*Micrococcus luteus* ATCC 10420 by agar diffusion. The protein nature of lactosporin was confirmed by its inactivation by proteolytic enzymes. Although lactosporin activity was pH dependent, it was stable when heated. The isoelectric point of lactosporin was in the range of 3.5-4.0.

In general, it is noted that *Bacillus coagulans* bacteriocins inhibit both gram-positive and gram-negative flora, as well as some putrefactive fungi of the genus *Fusarium*.

Normoflora, which present in the intestine, also protects the body from invasion of pathogenic microbes. Normoflora itself acquired various mechanisms of resistance to the action of destructive factors of the intestine. For example, by the formation of capsular polysaccharides on the surface of the cell wall. Normal microflora colonize in the intestine, occupying its entire free surface and, thereby, making pathogens physically impossible to attach.

Membrane flora through glycoconjugated receptors bind to the surface structures of the epithelium and enhances the production of mucus, thereby densifying the cytoskeleton of epithelial cells. The dominant flora competitively consumes all the necessary nutrients, and also releases bacteriocins—substances that inhibit the growth of microorganisms which come from outside environment.

As noted above, *Bacillus coagulans* do not remain in the human body forever, but leaves it 7 days after the last dose. Therefore, it does not violate the natural intestinal microbiocenosis, which was formed throughout the life of a particular person.

A number of clinical studies have shown that probiotics based on *Bacillus coagulans* not only do not suppress the normal intestinal flora, but also contribute to its restoration, when suppressed by antibiotics or in old age. In a study involving elderly patients with a reduced content of bifidobacteria and weakened immune defenses, the use of *Bacillus coagulans* significantly increased compared to baseline population of *Faecalibacterium prausnitzii* and bacteria of the genus *Bacillus*. It should be noted that this type of action was accompanied by the immunotropic and anti-inflammatory action of the probiotic, which, apparently, determined its positive effect on the normocenosis.

An immunomodulatory effect has been established for *Bacillus coagulans*. It has been proven in a number of experimental and clinical studies.

The immunomodulatory properties of *Bacillus coagulans* have been studied in experiments on mice and rats. Therefore, it was found that administration of bacterial powder to rats weighing about 200 g at a dose of 1 g per animal for 14 days caused a significant increase in the level of leukocytes in the blood compared to the control group. At the same time, the percentage of neutrophils and lymphocytes increased as well (Table 1). After administration of the probiotic in rats, the adhesion of neutrophils to nylon fibers also increased, which correlated with an increase in the number of neutrophils.

TABLE 1

Effect of *Bacillus coagulans* on the composition of rat blood white blood cells

| Leukocytes, % | Animal groups | |
|---|---|---|
| | Intuitive control | Introduction of *Bacillus coagulans* |
| Neutrophils | 48.5 ± 5.39 | 67.8 ± 2.95* |
| Lymphocytes | 35.83 ± 5.67 | 53.4 ± 2.19* |
| Monocytes | 7.67 ± 1.36 | 2.8 ± 1.30 |
| Basophils | 3.17 ± 0.98 | 2.4 ± 0.89 |
| Eosinophils | 4.84 ± 1.16 | 3.6 ± 1.51 |

*-significance of differences in relation to indicators of intact control ($P < 0.05$)

The ability of *Bacillus coagulans* to influence humoral immunity was found to cause an increase in the level of antibodies in the blood.

The stimulating effect of the probiotic on cellular immunity has been established in rats and mice in response to exposure to a T-dependent antigen. It was observed that preliminary administration of the probiotic notably decreased rat's feet thickness over time after administration of the BCG vaccine.

It was revealed a significant increase in the index of phagocytic activity in mice, which indicates a nonspecific immune response when they exposed to effect of *Bacillus coagulans*.

The obtained data indicate that *Bacillus coagulans* has a stimulating effect against both cellular and humoral immunity.

The scientific literature discusses the question of how probiotics exert their effects—is it active components of the cell wall or metabolites secreted by living bacteria. At present time these both mechanisms are currently experimentally confirmed.

Data from in vitro studies was reflecting effects of *Bacillus coagulans* on the immune system and on a free radical processes. In vitro experiments studies the effect of metabolites of living bacteria (supernatant) and an isolated cell walls was evaluated.

*Bacillus Coagulans* spores were activated by heating it to 70° C. for 30 minutes and incubated for 2 days at 37° C. in RPMI-1640 nutrient medium. The supernatant of living bacteria was obtained by centrifugation. To obtain fragments of the cell wall, the bacteria were destroyed by freezing—thawing, then the sediment was centrifuged and resuspended. The effect of bacteria on peripheral blood mononuclear and polymorphonuclear cells has been well documented.

It was found that the supernatant and the cell wall of bacteria inhibit the spontaneous formation of reactive oxygen metabolites in human polymorphonuclear leukocytes. The cell wall had a dose-dependent effect, and the supernatant showed a pronounced anti-inflammatory effect in low concentrations. The presence of a supernatant in a ratio of 1:1000 reduced the formation of reactive oxygen metabolites by 20% (p<0.004), and the cell wall caused a similar effect (a decrease of 30%) at a ratio of 1:10. Pre-incubation of polymorphonuclear cells with a supernatant and cell walls before reproduction of oxidative stress inhibited the formation of $H_2O_2$-induced reactive oxygen. Dilutions of 1:10 and 1:100 were effective.

The study of the effect on phagocytosis was carried out by the immunofluorescence method. Exposure of polymorphonuclear leukocytes with a supernatant at a 1:10 dilution significantly increased phagocytosis by 40%, and with cell walls in the same dilution by 25%. Incubation with a supernatant and cell walls at this concentration increased the population of polymorphonuclear leukocytes as a whole, with a number of cells in it being phagocytic, and the rest were not. Further dilution led to a decrease in the number of phagocytic cells.

The supernatant had a pronounced dose-dependent effect on the migration of polymorphonuclear leukocytes, and on both types of migration—spontaneous and directed (caused by chemotaxis). Directional migration was caused by three agents—the bacterial peptide f-MLP, the pro-inflammatory interleukin IL-8, and leukotriene LTB-4. When the supernatant was diluted 1:10, spontaneous migration increased by 300%. The cell walls caused a mild increase ofy 25%. Peptide-induced migration was increased by a 200% dilution in a 1:10 dilution, and 25% in the cell walls. Migration induced by interleukin-8 was suppressed by cell walls by 60%, and by supernatan to a slightly lesser extent. A pronounced dose-dependent effect was not observed. The leukocyte migration under the influence of B-4 leukotriene was also reliably suppressed by 60% by the bacterial cell walls at a dilution of 1:1000, and the supernatant had a less pronounced effect.

It was a highly pronounced dose-dependent effect of the supernatant and cell walls on the expression of killer cells. A significant increase was noted at dilutions of 1:400, 1:1600 and 1:6400. An increase in the content of the CD69 marker by 32% was observed with a dilution of the supernatant of 1:400, and by 36% with the same dilution of the cell walls.

The effect on the proliferation of T and B lymphocytes was not established during 5-day incubation. This indicates a lack of mitogenic potentials in the bacteria.

A study of the effect of *Bacillus coagulans* on cytokine production showed that both products suppressed IL-2 production, and increased production of IL-4, IL-10. In IL-6, a slight increase in TNF-α production was found, along with a significant increase in INF-γ.

Therefore, *Bacillus coagulans* has a pronounced anti-inflammatory effect, supported by the basic mechanisms of natural immunity. Activity during in vitro experiments is shown by both the cell wall of the bacterium and its metabolites. The manifestation of the identified types of activity is useful not only in terms of protecting the intestines from pathogens, but also in terms of anti-inflammatory effects, maintaining the integrity of the epithelium and normal digestion.

However, taking into account the fact that part of *Bacillus coagulans* entering the intestine is present in the form of spores, an important aspect of its interaction with elements of the immune system in this form. Data on direct experiments indicating an immunomodulatory effect of *Bacillus coagulans* spores have not been identified. However, for the most thoroughly studied bacteria, *Bacillus subtilis* (among bacteria of the genus *Bacillus*), it was shown that their spores are able to penetrate the lymphatic flow. It was confirmed that after a 5-days administration of spores to mice, they were found in Peyer's plaques and lymph nodes.

It is believed that spores of bacteria of this genus, having sizes of about 2 μm, can be captured by M-cells of the intestinal mucosa, which transfer them to Peyer's plaques and further to the lymph nodes. When administered orally to mice, spores elicited a systemic immune response in the form of an IgG subclass of IgG2a and a local response with a IgA release. An analysis of the intestinal immune system lymphocyte cytokine mRNA indicates early induction of interferon-γ, Th1 cytokine, and pro-inflammatory TNF-α cytokine.

In vitro experiments, mice macrophages efficiently phagocytosed the spores of *B. subtilis* from the culture medium. These spores can germinate inside the phagocyte and initiate the expression of genes responsible for the growth of the microorganism and protein synthesis. Meanwhile, such sprouted spores ceased to grow, and after about 5 hours were destroyed by lysis in the phagosomes of phagocytes. These studies are very important because they show that spores can interact with the intestinal lymphoid system, and this serves as a mechanism for stimulating the immune system. It also determines one of the mechanisms of action of probiotics.

Further evidence of the immunomodulatory effect of *Bacillus coagulans* is its clinically pronounced effect on arthritis in animals and humans. Results of a controlled clinical study of the effectiveness of this probiotic for arthritis are presented below (in the section of clinical studies in detail. However, given the leading role of the immune mechanisms in the development of arthritis, it can be concluded that *Bacillus coagulans* displays systemic anti-inflammatory and immunomodulating properties.

In recent years, the immunomodulating effect of *Bacillus coagulans* has been established in conditions of anti-biotic-associated diarrhea due to *Clostridium difficile*. This disease is one of the complications encountered in patients taking antibiotics. There is some evidence in the literature of the efficacy of the use of *Lactobacillus* spp probiotics in this disease. As well as *Saccharomyces boulardii*.

The molecular and immune mechanism of the development of this disease is currently understood as follows. *C. difficile* secretes toxins (mainly toxin A), which trigger the activation of three transcription factors. Nuclear factor kappa-B (NF-κB) promotes the production of chemokines and plays a role in apoptosis of colonocytes. Activator protein-1 (AP-1) is involved in the production of interleukin-8 (IL-8), which is caused by toxin A stimulation of colonocytes. An important point is the cAMP binding protein, which is necessary for the synthesis of prostaglandin E2, which in turn causes increased secretion of fluid and the occurrence of diarrhea, as well as stimulation of the production of Fas ligand and apoptosis of intestinal epithelial cells.

*Bacillus coagulans* in experimental studies has been shown to be effective in a mouse colitis model induced by *Clostridium difficile*. *Bacillus coagulans* (or normal saline in controlled group) was administered to mice orally at 2×109 CFU for 15 days. Pathology was caused by the introduction of a mixture of antibiotics from 5 to 8 days, clindamycin on day 10, and *C. difficile* culture at 104 CFU on day 11 of the experiment. The study showed that in the group administrated *Bacillus coagulans* no mice died, and in the control group, 2 animals died. On day 12, a significant (p=0.0002) difference was revealed between groups in the number of mice with normal stools—66.7% versus 13.0% in the control. On day 16, this figure was 23% and 0%, respectively. Intestinal microscopy showed that administration of *Bacillus coagulans* to mice significantly reduced the severity of pathological changes in the large intestine, such as, damages to crypts, edema, leukocyte infiltration. A decrease in the binding of the nuclear factor NF-κB and a decrease in the content of the chemokine MIP-2 to 16.3 against 24.6 pg/2 cm were also noted.

Similar results were obtained in a similar setting of the experiment with the introduction of vancomycin at a dose of 50 mg/kg for 6-10 days. Under the action of *Bacillus coagulans*, the consistency of the stool of mice was significantly improved. On day 17, it was normal in 88.9% of the animals of the experimental group and no improvement of pathology was observed in the control group. The activity of myeloperoxidase (a marker of the inflammatory process in the intestine) was significantly reduced—from 4.3 to 2.6 U/2 cm. Histological studies and the level of chemokine keratinocytes were significantly better.

The effects of *Bacillus coagulans* on the immune system when exposed to T cells with adenovirus and influenza A virus were studied in 10 healthy volunteers (mean age was 44 years old). The subjects took a probiotic in the form of capsules, 1 cap daily at a dose of 2×106 CFU for 30 days. Before taking the probiotic and upon its completion, blood samples from volunteers were taken and the level of cytokines after exposure of T cells with adenovirus and influenza A virus was determined in vitro. A significant increase in the production of tumor necrosis factor TNF-α in response to exposure to adenovirus and influenza A virus was observed at a rate 250% and 1709%, respectively, compared to baseline. This indicates that the immunomodulating properties of *Bacillus coagulans* can cause an increase in the T-cell response in viral infections.

The number of clinical studies have shown that probiotics based on *Bacillus coagulans* not only do not suppress the normal intestinal flora, but also contribute to its restoration, even when suppressed by antibiotics or in old age. So, in a study (see section Clinical experience) with elderly patients with a reduced content of bifidobacteria and weakened immune defenses, the use of *Bacillus coagulans* significantly increased compared to baseline population of *Faecalibacterium prausnitzii* and bacteria of the genus *Bacillus*. It should be noted that this type of action was accompanied by the immunotropic and anti-inflammatory action of the probiotic, which, apparently, determined its positive effect on the normocenosis.

*Bacillus coagulans* has an immunomodulatory effect, stimulating cellular and humoral immunity.

The metabolites possess an immunomodulatory effect, the metabolites secreted by the bacterium by the cell wall and spores of bacteria.

Based on the data available in the literature, it can be concluded that immunomodulating properties of *Bacillus coagulans* play a decisive role in pharmacological effects. This is indicated by the importance of the immune system in the pathogenesis of many diseases, and the sufficiency of even small amounts of a stimulant to have an effect (without the need for intensive reproduction of bacteria and colonization of the intestine). This is also indicated by experimental evidence of the penetration of bacteria and their spores into the lymphatic system and interactions with immunocompetent cells, as well as local and systemic immunotropic effects of the probiotic.

One of the ways to increase the speed of the onset of the immunomodulating and antiviral action of *Bacillus coagulans* spores is to strengthen their adhesive properties to the intestinal walls and activate their germination (sprouting). In order to enhance the adhesive properties of *Bacillus coagulans* and enhance the phagocytosis of spores, we proposed covalently chemically to modify spores surface to provide them an excessive negative charges. As a result of this modification, one third of the introduced spores will be absorbed by macrophages with corresponding immune responses.

In addition, irregular modification of surface structures leads to an increase in the diversity of surface charges. This is being simultaneously a method of combinatorial bioorganic synthesis, which will significantly increase the bioavailability of spores for different cells of the immune system. Such structures belong to a combinatorial derivatives. For the antiviral and probiotic properties of *Bacillus coagulans* to appear due to antagonism to pathogenic bacteria through the bacteriocin system, the bacterium must also be present in the intestine in a vegetative form.

To increase the percentage of germinated spores, we proposed the use of plant growth activators such as gibberellin. Such compounds were not previously used to stimulate the germination of spores, we are the first who studied them. More than a 10-fold increase in the percentage and rate of germination of spores was observed when these activators were added to the nutrient medium. The covalent modification of the surface of the spores did not affect their viability in any ways.

TERMINOLOGY

As used herein, the term "drug" encompasses drugs for use in both humans and animals in human medicine and veterinary medicine. In addition, the term "drug," as used herein, means any substance that provides a therapeutic and/or beneficial effect.

The definition of "drug", as used here, is not necessarily limited to substances that require permission to sell on the country's market, but may include substances that can be used in cosmetics, dietary supplements, food products (including food and drinks, for example), probiotic cultures, food additives, and naturally occurring drugs.

In addition, the term "drug", as used here, encompasses a product intended for inclusion in animal feed, for example, livestock feed and/or pet food. As used here, the improvement of the intestinal microbiota "refers to an increase in the number and/or type of microorganisms present in the intestines of the host, and/or an increase in the activity of these microorganisms in terms of their metabolic, structural, protective and other useful functions.

As used herein, the term "innate immune system", also known as a non-specific immune system, includes cells and mechanisms that provide the host with immediate protection against infection by other organisms in a non-specific way. This means that the cells of the innate system recognize pathogens and respond to them genetically, but unlike the adaptive immune system, it does not provide the owner with a long-term or protective immunity.

As used herein, the term "regulation of the innate immune system" means inducing the activity of the innate immune system and/or increasing the level of activity relative to the initial level of activity, so that it promotes immune homeostasis. As used herein, the term "adaptive immune system", otherwise known as "specific immune system", refers to highly specialized system cells and processes that eliminate or prevent the growth of pathogens.

An adaptive immune response gives the vertebral immune system the ability to recognize and recall specific pathogens (for the formation of immunity), and prepare them for stronger attacks every time it encounters a pathogen. Used herein, the term "regulation of the adaptive immune system"

means the induction of activity of the adaptive immune system and/or stimulation relative to the initial level of activity.

Preferably, the adaptive immune system undergoes modulation in the direction of immunoregulation (and not activation of the immune system, therefore, reducing inflammation). Defects and disorders associated with the adaptive immune system, in particular those associated with the functioning of T cells, are associated with many inflammatory and autoimmune diseases. T-cell reactions associated with Th1, Th2, and Th17 are associated with topical, inflammatory, and autoimmune diseases.

Therapies that improve or increase regulatory T-cell populations are important in controlling diseases triggered by excessive T-cell responses associated with Th1, Th2, and Th17. Forms of diarrhea that can be treated prophylactically and/or therapeutically in accordance with the invention include acute diarrhea and chronic diarrhea. In certain embodiments, the diarrhea that is treated in accordance with the invention is diarrhea of an infectious nature that is caused by a viral, bacterial or parasitic pathogen.

In other embodiments, diarrhea that is treated according to the cause is non-infectious diarrhea. Non-infectious diarrhea can be, for example, diarrhea caused by food intolerance, diarrhea caused by a fatty diet, diarrhea caused by alcohol, diarrhea caused by a psychological factor, diarrhea caused by the administration of a drug, diarrhea caused by the use of a therapeutic procedure, diarrhea associated with a disease or with a clinical condition, or diarrhea associated with drug withdrawal.

The term "probiotic strain" in this description is intended to refer to a strain of a living microorganism that has a beneficial effect on the health of the host. As a rule, the owner is a person, but it can be assumed that the owner may be another mammal, for example a dog, cat, ruminant, namely a sheep, goat, calf, cow, deer, camel, horse, wild boar, in particular pigs and piglets, leporids (hare), murid (mouse) and rodents of the Caviidae family (mumps).

The strain tested using the method according to the invention may be any strain of the microorganism. In certain embodiments, the test strain could be an yeast strain. Among the yeast that can be tested, we can point it out for example, yeast of the genus *Saccharomyces*, in particular the species *Saccharomyces boulardii*, *Saccharomyces cerevisiae*, the yeast of the genus *Kluyveromyces*, in particular the species *Kluyveromyces marxianus*. In other embodiments, the test strain is a bacterial strain.

The test strain is preferably selected from bacteria recognized as safe for humans and/or animals. Among the bacteria that can be tested, for example are, bacteria of the genus *Bifidobacterium*, in particular the species *Bifidobacterium animalis*, *Bifidobacterium bifidum*, *Bifidobacterium infantis*, *Bifidobacterium lactis*, *Bifidobacterium longum* and *Bifidobacterium breve*; bacteria of the genus *Lactobacillus*, in particular kinds of *Lactobacillus reuteri*, *Lactobacillus acidophilus*, *Lactobacillus bulgaricus*, *Lactobacillus brevis*, *Lactobacillus casei*, *Lactobacillus helveticus*, *Lactobacillus johnsonii*, *Lactobacillus plantarum*, *Lactobacillus paracasei*, *Lactobacillus rhamnosu* and *Lactobacillus salivarius*; bacteria of the genus *Weisella*, in particular species *Weisella cibaria*, *Weisella kimchii*, *Weisella thailandensis*; bacteria of the genus *Bacillus*, in particular species of *Bacillus subtilis*, *Bacillus coagulans*, *Bacillus amyloliquefaciens*, *Bacillus licheniformis*, *Bacillus cereus* and *Bacillus clausii*; bacteria of the genus *Lactococcus*, in particular the species *Lactococcus lactis*; bacteria of the genus *Enterococcus*, in particular *Enterococcus faecium*, *Enterococcus fecalis*; bacteria of the genus *Streptococcus*, in particular the species *Streptococcus thermophilus*; bacteria of the genus *Escherichia*, in particular the species *Escherichia coli*.

A "sporulating form" of a bacterium refers to the form of a bacterium placed in adverse conditions. The spores of each of the probiotic bacteria according to this research can be covalently chemically modified at surface antigens to increase adhesive properties. Therefore, the sporulating form is a stable form that allows bacteria to withstand adverse environmental conditions, for example, lack of nutrients, i.e., limiting nutrient medium, lack of water, wide fluctuations in pH or temperature, or passage through the digestive tract. Adverse conditions for bacterial cells are created, for example, by not updating the culture medium of bacteria, stopping the supply of nutrients to the culture medium, using a limiting nutrient medium, changing the temperature, changing the pH value or their combination.

The method for producing *Bacillus coagulans* cells may also comprise an additional process of drying the cells to obtain *Bacillus coagulans* cells in dry form. The expression "*Bacillus coagulans* cells in dry form" means that the biomass obtained at the end of this method for producing *Bacillus coagulans* cells contains more than 90% dry matter, preferably more than 95% dry matter. Drying is, for example, lyophilization drying, vortex spray drying or spray drying.

Forms of Diarrhea.

"Acute diarrhea" means diarrhea whose symptoms last for less than two weeks, and "chronic diarrhea" means diarrhea whose symptoms last for at least two weeks, preferably at least one month. Acute diarrhea includes, for example, viral gastroenteritis, bacterial gastroenteritis and food intoxication (e.g. *salmonellosis*, shigellosis, *Staphylococcus aureus* infections, *Bacillus cereus* infections, *Escherichia coli* infections).

Chronic diarrhea includes, for example, reduced absorption syndrome, gastroenteropathy (celiac enteropathy, Whipple's disease, Crohn's disease, etc.), motor diarrhea (i.e. diarrhea as a result of the passage of contents through the intestines), secretory diarrhea (i.e. diarrhea resulting from the acceleration of water-electrolyte secretion in the small intestine and/or colon), osmotic diarrhea (i.e. diarrhea resulting from the presence of dissolved substances in the gastrointestinal tract that are poorly absorbed and cause osmosis effect).

Other types of diarrhea that can be treated with a probiotic strain according to the invention or cells obtained by cultivating a probiotic strain according to the invention include diarrhea resulting from anxiety or intense emotions, diarrhea resulting from food intolerance (e.g. lactose of cow's milk, sorbitol, gluten and etc.), diarrhea resulting from certain types of treatment, for example, treatment with magnesia, radiotherapy or chemotherapy, or some types of surgical intervention, for example, gastrectomy or ileum resection, diarrhea resulting from overflow or irritation of the stomach, intestines, colon, etc., diarrhea resulting from the withdrawal of certain substances, such as heroin, diarrhea resulting from the use certain medicines, such as antibiotics.

Other examples of diarrhea that can be treated with a probiotic strain according to our research study or cells obtained by culturing a probiotic strain according to the invention include diarrhea accompanying an attack of spillage of bile or indigestion, diarrhea resulting from excessive consumption of certain laxative foods, and diarrhea of runners. In some preferred embodiments, the diarrhea that is treated with the probiotic strain of the invention or cells obtained by cultivating the probiotic strain of the invention is not diarrhea caused by the administration of an antibiotic or, more generally, the administration of a drug. In other preferred embodiments, diarrhea that is treated with a probiotic strain of the invention or cells obtained by culturing a probiotic strain of the invention is not infectious diarrhea.

The closest prototype of the current invention are sweet and healthy compositions containing at least one prebiotic and one probiotic (U.S. Pat. No. 9,114,169 B2). *B. coagulans* and *S. boulardii* are also considered probiotics. The disadvantage of the invention is the lack of a significant prophylactic effect on the composition against respiratory viruses, in particular influenza, due to the absence of covalent chemically modified spores of *B. coagulans*. While in our application it was shown that covalent modification of spores can increase their immunomodulatory effect by several times due to an increase in their adhesion to phagocyte receptors and intestinal epithelium, which increases the percentage of spores subjected to germination. Also in our composition there are activators of spore germination: gibberellin, para-aminobenzoic acid; carnitine; auxin or its derivative. Previously, these substances were known as activators—stimulants of plant growth, seed germination, but were not known as activators of bacterial spore hatching, especially in food/cosmetic compositions. The combined use of modified spores with germination activators significantly enhances the immunomodulatory and antiviral effects of the composition. The thermal stability of all components allows you to include them both in hot and cold drinks, toothpastes and food additives. In addition, benzylisoquinoline derivatives (papaverine) or the raw materials containing them (poppy seeds) are included in the composition. These substances have the ability to accelerate the growth of probiotics, increase the degree of colonization of the intestine, which reduces the time of onset of positive immunotropic and antiviral effects by several times.

DISCLOSURE OF INVENTION

The basis of the invention is the task to develop a food, cosmetic and pharmaceutical composition with a powerful immunomodulating and protective antiviral effect.

The problem is solved due to the fact that it is proposed to include in the food, cosmetic and pharmaceutical compositions containing a mixture of probiotics with an immunomodulating effect, among probiotics, including modified spores of the saprophytic probiotic bacterium *B. coagulans*. *B. coagulants* surface is covalently chemically modified with different degrees the surface of which is covalently chemically modified with varying degrees of modification by acylating and alkylating modifiers, this composition may also additionally include compounds of the benzylisoquinoline group or raw materials containing them, plant extracts with glycosides, and also include at least two of the following components: gibberellin, para-aminobenzoic acid; carnitine; auxin or its derivative. At the same time, the degree of surface modification of the spores of the saprophytic probiotic bacterium *B. coagulans* is an amount up to 300%, calculated on the weight of the spores after drying.

The covalent chemical modification of spores of the saprophytic probiotic bacterium *B. coagulans* is represented by acylation of dicarboxylic and polycarboxylic acids anhydrides or halides. Also, spore modifications can be carried out through the alkylation process with halogen derivatives of carboxylic and polycarboxylic acids.

In another invention instead of probiotics, the composition may contain saprophytic probiotic fungus *S. boulardii* in an amount of from 1 to 10 lg CFU/ml per dose of the product. The composition may also include a plant extract with glycosides licorice extract in an amount from 0.05% to 0.5% by weight of the product. In another implementation of the invention, the composition may also include, as a plant extract with glycosides, *stevia* extract in an amount of from 0.05% to 0.5%.

The composition may also include, as a plant extract with glycosides, *spirulina* extract in an amount from 0.05% to 5% by weight of the product and/or alfalfa extract in an amount of from 0.05% to 5% by weight of the product. In another implementation of the invention, the composition is characterized and different by the amount of the probiotic bacterium *B. coagulans* is from 1 to 10 lg CFU/ml per dose of the product. The composition may also differ by the raw material containing compounds of the benzylisoquinoline group, which represents crushed ripe poppy seeds or an extract of ripe poppy seeds, or papaverine.

The composition may also contain gibberellin spore germination activators in an amount of 0.01-0.05% by weight of the product. The composition of another implementation of the invention may contain para-aminobenzoic acid in an amount of 0.01-0.5% by weight of the product. The composition of another implementation of the invention may contain carnitine in an amount of 0.1-1.0% by weight of the product. The composition may also contain auxin or its derivative in an amount of 0.01-0.05% by weight of the product.

EXAMPLES

The following examples describe some embodiments of the current invention. However, it should be taken in to consideration that these examples are for illustration purposes only and do not in any way limit the scope of the invention.

Example 1. Obtaining Covalent Chemically Modified Spores of *B. coagulans* (KCMS)

Any Probiotic Strain of *B. coagulans* can be Used to Obtain Spores.

1. Inoculate the culture, for example, strains of *Bacillus coagulans* MTCC 5856, *Bacillus coagulans* ATCC 31284, *Bacillus coagulans* NBRC 3887, *Bacillus coagulans* ATCC 7050 or any other in 1.0 liter of broth yeast extract with glucose and acetate (HiMedia, Mumbai, India) or MRS broth nutrient medium containing 0.5% Tween-80, or in an environment based on corn extract powder and incubated at 37° C. for 24-48 hours;

2. After incubation and accumulation of bacterial biomass in the first stage the temperature reduced of the cultivated medium to 5° C. and carry out incubation at this temperature for 24-48 hours. At the same time, there is complete sporulation of all bacteria in the nutrient medium due to the temperature-negative bacteria conditions.

3. The nutrient medium is centrifuged at 20 g for 2 hours, the spore precipitate is washed twice with distilled water. A spore suspension is obtained in a ratio of dry sediment to water of 1:100. As a result of the suspension containing purified spores, residual nitrogen is determined and converted to protein by any classical method known to a person skilled in the area.

4. Dry succinic anhydride is added to the spore suspension in an amount up to 300% by weight of dry spores (for example, 300 mg of succinic anhydride is added per 100 mg of dried spores) and the solution is stirred until the precipitate of succinic anhydride is completely dissolved. Modification of more than 300% of the dry mass of spores leads to a loss in spores of viability and ability to germinate, they completely die. Instead of succinic anhydride, other carboxylic and polycarboxylic acid anhydrides and halides may be used. Instead of the acylation process with succinic anhydride, an alkylation process using haloalkanes or halogen derivatives of carboxylic and polycarboxylic acids can be used. Modification should lead to an increase in the total negative charge of the spore surface. This enhances the adhesion of spores to the intestinal wall, enhances the phagocytosis of such spores by macrophages and causes a more active immune response in shorter terms.

5. Next, the modified spore solution is lyophilized or dried on a tray at a temperature of up to 40° C. and then used to obtain the composition according to the claimed invention.

Example 2. Obtaining a Composition Based on Covalent Chemically Modified Spores of *B. Coagulans* (KCMSB) for Inclusion in Food, Cosmetic and Pharmaceutical Products By using any mixer for solid compositions, we will conduct the manufacturing of the composition according to the invention. Dry KCMSB with an activity of 1-50 lg CFU/g is added to the mixer, dry lyophilized powder *S. boulardii* is added in an amount of 1 to 50 lg CFU/g, licorice extract is added in an amount of 0.05% to 0.5% of the total the weight of the composition, add *Stevia* extract in an amount of from 0.05% to 0.5% of the total weight of the composition, add *spirulina* extract in an amount of from 0.05% to 5% of the total weight of the composition, add alfalfa extract in an amount of from 0.05% to 5% by weight of the product, add crushed mature poppy seeds or poppy extract or papaverine in an amount of from 0.05% to 5% by weight of the composition, add gibberellin in an amount of 0.01-0.05% by weight of the composition, add carnitine in an amount of 0.1-1, 0% by weight of the composition. Also, in addition to gibberellin and carnitine, the composition may include para-aminobenzoic acid in an amount of 0.01-0.5% by weight of the composition and auxin or its derivative in an amount of 0.01-0.05% by weight of the composition. The mixed composition is mixed in a mixer until it smooth and used in the future to obtain food and pharmaceutical compositions, toothpaste and cosmetic creams.

Determination of Germination Rate of *B. coagulans* (BC) Spores

KCMSB in the form of a suspension in the amount of 0.1 g/1 ml of distilled water is applied to the surface of six Petri dishes with Lacto medium. A similar procedure is carried out with different KCMSB compositions (presented in Table 1), 6 Petri dishes per sample. Unmodified spores are applied to the last group of Petri dishes. Every 3 hours, a smear sample is taken, stained according to Gram and the presence and quantity of colony forming units—vegetative sprouted forms of *Bacillus coagulans* (BC)—are determined. The results are presented in table 2.

TABLE 2

Results of determining the rate of KCMSB germination in comparison with unmodified *Bacillus coagulans* spores

| Group No. | The name and composition spores | The time of appearance of the first colonies | 1 g CFU/ml 72 hours later |
|---|---|---|---|
| 1. | Lactovit-Forte (unmodified spores) | 72 ± 5 | 15 ± 5 |
| 2. | KCMSB (option with poppy seed extract) | 36 ± 2* | 85 ± 12* |
| 3. | KCMSB (papaverine variant) | 36 ± 6* | 90 ± 16* |
| 4. | KCMSB (poppy extract variant, gibberellin, carnitine)) | 24 ± 4* | 90 ± 15* |
| 5. | KCMSB (modified disputes only) | 48 ± 3* | 65 ± 10* |

*P < 0.01, the difference is significant against the control of group 1

As can be seen from table 2, the germination of vegetative forms of BC from all HCMSB compositions is statistically significantly faster than the control. At 72 hours of incubation in the control, only 15 lg CFU/ml of CD is observed, whereas in the experimental groups this indicator is 6 to 9 times higher. This indicates that the components of HCMSB compositions stimulate germination of CD spores and stimulate further growth of germinated bacteria. The absence of benzylisoquinolines (papaverine) in the composition leads to less effective stimulation of CD growth, although it is higher than the control (65±10 lg CFU/ml)

Example 3. Obtaining Food, Cosmetic and Pharmaceutical Products Based on the Composition of Example 2

Food Composition

Initially, the core of the product is the composition of Example 2. The amount of which varies in the product from 0.1% to 30% by weight of the product. The introduction of less than 0.1% does not allow the composition to show its antiviral and immunomodulating properties, more than 30% of the activity of the product does not increase, which is not rational.

The composition of the invention may be a food composition, a bioactive food supplement, or a pharmaceutical composition. Food composition means any type of product, drink or confectionery. The food composition, for example, may be a beverage, briquetted cereal concentrate, chewing gum, chocolate, or a dairy product such as a dairy product made by fermentation of a plant product.

Also, the proposed composition can be introduced into cold and hot drinks, sweet foam in aerosol cans, ice cream, cookies, yogurts, cakes, sweets, kielbasa, sausages, dry mixes for feeding children, beer drinks and low alcohol drinks, toothpastes, creams. "Bioactive food supplement" means a food product whose purpose is to supplement a normal diet.

A bioactive nutritional supplement is a concentrated source of nutrients or other substances having a nutritional or physiological effect, alone or in combination. The bioactive nutritional supplement is supplied to the market in a dosage form, namely in such dosage forms as a capsule, lozenge, tablet, pill and other similar forms, sachets with powder, ampoules with liquid, vials equipped with a dropper, and other similar forms of liquid or powder preparations, which are intended for use in measured units of a small amount. The composition may also include amino acids: glycine, arginine, lysine, taurine, phenylalanine or mixtures thereof and any other amino acids.

The composition may also include vitamins: ascorbic acid, thiamine, riboflavin, rutin, folic acid, cyanocobalamin, or a mixture thereof, as well as any other vitamin. The composition may also contain extracts of green or black tea, or any other plant extract used in the food industry. The composition according to the invention, for example, is suitable for daily consumption of cells obtained by culturing a probiotic strain in an amount of from $1\text{-}10^8$ CFU to $1\text{-}10^{11}$ CFU, preferably in an amount of from $1\text{-}10^9$ CFU to $1\text{-}10^{10}$ CFU, when intended for human consumption.

The composition according to the invention, for example, is suitable for daily use of cells obtained by culturing a probiotic strain in an amount of from $1\text{-}10^5$ CFU to $1\text{-}10^{11}$ CFU, preferably in an amount of $1\text{-}10^6$ CFU to $1\text{-}10^{10}$ CFU, when it is intended veterinary applications. The term CFU denotes a colony forming unit.

Probiotics are preferably administered as an oral composition containing metabolically active ones, i.e. probiotic organisms, living and/or lyophilized or non-viable, heat-killed, irradiated or lysed, in the form of spores or covalently chemically modified spores.

The probiotic composition described herein can be administered orally in the form of a tablet, capsule or powder. Additionally, the probiotic composition may be administered orally as a food or nutritious product, such as milk or whey-based fermented milk product or as a pharmaceutical product.

In accordance with one embodiment of the invention, the composition is an edible product, such as a dairy product, a drink, juice, soup or baby food. A probiotic may optionally be combined with at least one suitable prebiotic compound.

Prebiotic "is usually a non-digestible carbohydrate, such as an oligo- or polysaccharide or alcohol sugar, which is not destroyed or absorbed in the upper part of the digestive tract. Known commercially available prebiotics include inulin, fructo-oligosaccharides, oligofructose or galacto-oligosaccharides.

The term "edible product" is intended to encompass all consumed products, especially food products, and may be solid, jelly-like, or liquid. This term covers both finished products and products that are produced by using the probiotic composition as a starter only or in combination with conventional starter cultures or other probiotics. Food products may, for example, be products of the dairy industry or the beverage industry. Alternatively, it may be a natural product.

Initially, the core of the product is the composition of Example 2. The amount of which varies in the product from 0.1% to 30% by weight of the product. The introduction of less than 0.1% does not allow the composition to show its antiviral and immunomodulating properties, more than 30% of the activity of the product does not increase, which is not rational.

In the context of the present invention, "physiologically acceptable diluent or excipient" means any medium or additive that does not affect the effectiveness of the biological activity of the active component (in this case, yeast or bacterial cells), and which is not too toxic to the patient or subject at the administered concentrations.

A physiologically acceptable diluent or excipient may be a diluent or excipient suitable for administration to humans and/or animals (in particular mammals). The pharmaceutical compositions of the present invention may be administered using any effective combination of dosage and route of administration in order to obtain the desired therapeutic effect. Exact amount, intended for administration, may vary from patient to patient, depending on the age, weight and general health of the patient, the origin and severity of diarrhea, etc. The method of administration (oral or parenteral) may be selected depending on the origin of diarrhea and/or depending on the age and/or health of the patient.

By way of example, the invention relates to the pharmaceutical composition as defined above for daily use of cells obtained by culturing said probiotic strain in an amount of $1\text{-}108$ CFU to $1\text{-}10^{11}$ CFU, preferably in an amount of $1\text{-}10^9$ CFU to $10^{10}$ CFU, in when it is intended for human consumption.

The present invention also relates to the pharmaceutical composition described above, which is intended for daily use of cells obtained by culturing said probiotic strain in an amount of $1\text{-}10^5$ CFU to $1\text{-}10^{11}$ CFU, preferably in an amount of $1\text{-}10^6$ CFU to $1\text{-}10^{10}$ CFU, when it is intended for use in veterinary medicine.

The composition of the pharmaceutical composition according to the present invention may vary depending on the route of administration and dosage in which the composition will be used. After being formulated with at least one physiologically acceptable diluent or excipient, the pharmaceutical composition of the invention may be in any form suitable for administration to a mammal, in particular humans, for example, in the form of lozenges, tablets, sugar coated tablets, capsules, syrup, ointments, injectable solutions, suppositories, etc.

A person skilled in the art knows how to select the most suitable diluents and excipients for preparing this type of composition. Thus, for example, excipients such as water, 2,3-butanediol, Ringer's solution, isotonic sodium chloride solutions, synthetic mono- or diglycerides and oleic acid are often used in the preparation of injectable forms.

Liquid compositions, including emulsions, microemulsions, solutions, suspensions, syrups, elixirs, etc., can be formulated in the presence of solvents, solubilizers, emulsifying agents, oils, fatty acids and other additives such as suspending agents, preservatives, sweeteners, flavoring agents, viscosity-modifying agents, coloring agents, etc.

Solid compositions intended for administration by oral route can be formulated in the presence of an inert excipient such as sodium citrate, and optionally such additives as binders, wetting agents, disintegrants, absorption enhancers, lubricants, etc. In certain embodiments, the pharmaceutical composition of the present invention is formulated to immediately release the active (active) component or active components, in particular yeast cells or bacterial cells obtained by culturing a probiotic strain. Alternatively, a pharmaceutical composition may be provided for the purpose of prolonged or targeted release of the active component or active components or to protect the active component or active components, for example, from intragastric acidity and enzymes. For this purpose, coatings that are resistant to pH and/or gastric enzymes, coatings that are sensitive to pH and/or enzyme activity, or bioadhesive coatings that adhere to the walls of the stomach or intestines, or encapsulation systems can be used.

In addition, the pharmaceutical compositions of the present invention may contain at least one additional active pharmaceutical ingredient (i.e., in addition to yeast or bacterial cells obtained by culturing a probiotic strain). "Active pharmaceutical ingredient" means any compound or substance whose administration has a therapeutic or beneficial effect on the health condition or general condition of the patient or subject to which it is administered.

Thus, the active pharmaceutical ingredient may be active in preventing or treating diarrhea by administering a pharmaceutical composition; may be active against a condition or symptom associated with diarrhea (e.g., fever, vomiting, or abdominal cramps); or may increase the availability and/or activity of the active component or active components of the pharmaceutical composition.

Examples of active pharmaceutical ingredients that may be present in the composition of the present invention include, without limitation, anti-inflammatory drugs, antibiotics, antipyretics, anti-emetics, antihistamines, vitamins, antispasmodics, etc. In an advantageous embodiment, the other active pharmaceutical ingredient is not a *Bacillus coagulans* strain or cells obtained by culturing such a strain, preferably it is not a bacterial strain or cells obtained by culturing such a strain, more preferably it is not a probiotic strain or cells obtained by culturing such a strain. An example of a pharmaceutical composition according to the present invention is a composition containing yeast or bacterial cells obtained by culturing a probiotic strain as the sole active pharmaceutical ingredient. Unless otherwise defined, all technical and scientific terms used in the description have the same meaning as is generally understood by one of ordinary skill in the art to which the invention pertains. Moreover, all publications, patent applications, all patents and all other references made in the description are included in the description by reference.

In an advantageous embodiment, the other active pharmaceutical ingredient is not a *Bacillus coagulans* strain or cells obtained by culturing such a strain, preferably it is not a bacterial strain or cells obtained by culturing such a strain, more preferably it is not a probiotic strain or cells obtained by culturing such a strain. An example of a pharmaceutical composition according to the present invention is a composition containing yeast or bacterial cells obtained by culturing a probiotic strain as the sole active pharmaceutical ingredient. Unless otherwise defined, all technical and scientific terms used in the description have the same meaning as is generally understood by one of ordinary skill in the art to which the invention pertains. Moreover, all publications, patent applications, all patents and all other references made in the description are included in the description by reference.

TABLE 3

Products in which the inclusion of our composition is promising

| № p/p | Product | Additional specific qualities | New consumer qualities |
|---|---|---|---|
| 1. | Cold drink (carbonated, non-carbonated) | Activator of metabolism and energy of the body | It prevents intestinal upsets (including from viral rota- and coronavirus enteritis), protects against colds (including flu), activates the immune system, reduces or removes allergic reactions, improves the absorption of basic food components (proteins, carbohydrates, vitamins, fats). It activates the body's metabolism due to the stimulation of tissue respiration and due to the synergism of the components. |
| 2. | Hot drink (coffee, tea) | Activator of metabolism and energy of the body | |
| 3. | Briquetted Grain Concentrate | | |
| 4. | Chewing gum | Prevents disturbance of the microflora of the oral cavity and caries | |
| 5. | Chocolate | | |
| 6. | Milk product | | |
| 7. | Fermented milk product | | |
| 8. | Sweet foam in aerosol cans | | |
| 9. | Ice cream | | |
| 10. | Cookies | | |
| 11. | Candies | | |
| 12. | Yoghurts | | |
| 13. | Cakes | | |
| 14. | Dry food mixes for children | Increases weight gain, prevents bowel disease | |
| 15. | Dry protein mixes for athletes | Increases weight gain, prevents bowel disease | |
| 16. | Sausages of different kind (kielbasa, sardelka, sosiska) | | |
| 17. | Beer drinks | | |
| 18. | Mild alcohol drinks | Compensates for immunodeficiency caused by alcohol by the immunomodulatory effect of the composition | |
| 19. | Toothpastes | | Prevents tooth decay, activates local immunity in the oral cavity, protects against tonsillitis, scarlet fever, stomatitis (including viral), supports general immunity in tone |
| 20. | Cosmetic creams | | Normalizes skin turgor and local immunity, promotes wound healing after sunburn. |

TABLE 3-continued

Products in which the inclusion of our composition is promising

| № p/p | Product | Additional specific qualities | New consumer qualities |
|---|---|---|---|
| 21. | Bioadditives (capsule, lozenge, tablet, pill and other similar forms, sachets of powder, ampoule with liquid, bottles equipped with a dropper) | Enhances weight gain (for athletes and for patients in the rehabilitation phase), improves food absorption | Components for preventing viral and microbial pathologies against the background of immunodeficiency and a means for the comprehensive correction of pathologies caused by impaired immune functions. They can be promising as a Components supplements of sports nutrition with properties to stimulate the body's metabolism and energy (endurance). |

Toothpastes and Cosmetic Creams

Initially, the core of the product is the composition of Example 2. The amount of which varies in the product from 0.1% to 30% by weight of the product. The introduction of less than 0.1% does not allow the composition to show its antiviral and immunomodulating properties. However, more than 30% of the activity of the product does not increase, which is not rational. In some embodiments, probiotics release profiles for microorganisms may be controlled, such as, but not limited to, *Bacillus coagulans, Bacillus subtilis, Bacillus laterosporus, Bacillus laevolacticus, Sporolactobacillus inulinus, Lactobacus lactobacillus bacillus acidophilus, Lactobacus bacillus bacillus acidophilus Lactobacillus fermentum, Lactococcus lactis, Pedioccocus acidilacti, Pedioccocus pentosaceus, Pedioccocus urinae, Leuconostoc mesenieroides, Bacillus coagulans, Bacillus subtilis, Bacillus laterosporus, Bacillus laevolacticacus*, Spor. Breath fresheners are also known under the following trademarks: Retsyn™, Actizol™ and Nutrazin™. Examples of odor control compositions are also described in U.S. Pat. No. 5,300,305 to Stapler et al., And in Patent Publications No. US 2003/0215417 and 2004/0081713, which are incorporated herein by reference for all purposes.

Dental care ingredients (also known as oral care ingredients) may include, but are not limited to, tooth whiteners, stain removers, oral cleansers, whitening agents, desensitizing agents, tooth remineralizing agents, antibacterial agents, anticariotic agents, buffering agents to neutralize plaque acids, surfactants and anti-tartar agents. Non-limiting examples of such ingredients may include hydrolytic agents, including proteolytic enzymes, abrasives such as hydrated silicon dioxide, calcium carbonate, sodium bicarbonate and alumina, other stain removing active ingredients, such as surfactants containing but not limited to anionic surfactants such as sodium stearate, sodium palmitate, sulfonated butyl oleate, sodium oleate, fumaric acid salts, glycerin, hydroxylated lecithin, sodium lauryl sulfate, and chelating agents such as polyphosphates, which are commonly used as anticalculus ingredients.

In some embodiments, dentifrice ingredients may also include tetrasodium pyrophosphate and sodium tripolyphosphate, sodium bicarbonate, sodium acid pyrophosphate, sodium tripolyphosphate, xylitol, sodium hexametaphosphate. In some embodiments, peroxides are provided, such as carbamide peroxide, calcium peroxide, magnesium peroxide, sodium peroxide, hydrogen peroxide and peroxydisphosphate. In some embodiments, potassium nitrate and potassium citrate are provided.

Other examples may include casein-glycomacropeptide, calcium casein peptone derivative—calcium phosphate, casein phosphopeptides, casein phosphopeptide—amorphous calcium phosphate (CPP-ACP), and amorphous calcium phosphate. Other further examples may include papain, krillase, pepsin, trypsin, lysozyme, dextranase, mutanase, glycoamylase, amylase, glucose oxidase, and combinations thereof.

Additional examples may include surface active substances, such as sodium stearate, sodium ricinoleate and sodium lauryl sulfate, as a surface active substances for use in some embodiments to achieve enhanced prophylactic action, and to make dental care ingredients more acceptable in cosmetic dentistry. Surface active substances may be used preferably as detergents that impart detergent and foaming properties to the composition.

Suitable examples of surfactants are water-soluble salts of higher aliphatic monoglyceride monosulfates monosulfates, such as the sodium salt of monosulfonated fatty acid monoglycerides of hydrogenated coconut oil, higher alkyl sulfates, such as lauryl sulfate sodium alkylaryl sulfonates such as sodium dodecylbenzenesulfonate, higher alkyl sulfoacetates, sodium lauryl sulfoacetate, esters of higher aliphatic acids and 1,2-dihydroxypropanesulfonate, and substantially saturated higher aliphatic acylamides of lower amino aliphatic acids such as having from 12 to 16 carbon atoms in fragments of an aliphatic acid, alkyl or acyl radicals, and the like. Examples of the latter amides mentioned are N-lauroylsarcosine, and the sodium, potassium and ethanolammonium salts of N-lauroyl, N-myristoyl or N-palmitoylsarcosine.

In addition to surfactants, dentifrice ingredients may include antibacterial agents, such but not limited to triclosan, chlorhexidine, zinc citrate, silver nitrate, copper, limonene, and cetylpyridinium chloride. In some embodiments, additional anticariotic agents may include fluoride ions or fluorine-containing components, such as inorganic fluoride salts.

In addition to surfactants, dentifrice ingredients may include antibacterial agents, such but not limited to triclosan, chlorhexidine, zinc citrate, silver nitrate, copper, limonene, and cetylpyridinium chloride. In some discussion, additional anticariotic agents may include fluoride ions or fluorine-containing components, such as inorganic fluoride salts. In some embodiments, a fluorine-containing compound can also be included as an ingredient, which has a beneficial effect on oral care and hygiene, for example, to reduce the solubility of enamel in acid and protect teeth from decay. Examples thereof include sodium fluoride, stannous fluoride, potassium fluoride, potassium stannous fluoride (SnF2-KF), sodium hexafluorostannate, stannous chlorofluoride, sodium fluorozirconate and sodium monofluorophosphate. In some embodiments, urea is included.

Pharmaceutical Compositions

Various methods for preparing a patentable pharmaceutical composition (PFC) can be used in addition to the methods described in Examples 1 and 2.

The PFC composition can be given orally or can be administered by intravascular, subcutaneous, intraperitoneal injection, in the form of an aerosol, by ocular route of administration, into the bladder, topically, and so on. For example, inhalation methods are well known in the art. The dose of the therapeutic composition will vary widely depending on the particular antimicrobial PFC administered, the nature of the disease, frequency of administration, route of administration, clearance of the agent used from the host, and the like. The initial dose may be higher with subsequent lower maintenance doses.

The dose can be administered with a frequency of once a week or once every two weeks, or divided into smaller doses and administered once or several times a day, twice a week, and so on to maintain an effective dose level. In many cases, a higher dose will be needed for oral administration than for intravenous administration. PFCs can be included in many therapeutic compositions. More specifically, the PFCs of the present invention can be incorporated into pharmaceutical compositions in combination with suitable pharmaceutically acceptable carriers or diluents, and can be incorporated into preparations in solid, semi-solid, liquid or gaseous forms, such as capsules, powders, granules, ointments, creams, foams, solutions, suppositories, injections, forms for inhalation applications, gels, microspheres, lotions and aerosols. As such, the administration of the compounds can be carried out in various ways, including oral, buccal, rectal, parenteral, intraperitoneal, intradermal, transdermal, intratracheal administration and so on.

The PFCs of the invention can be distributed systemically after administration or can be localized using an implant or other composition that holds the active dose at the site of implantation. The PFCs of the present invention can be administered alone, in combination with each other, or they can be used in combination with other known compounds (e.g. clopidogrel, anti-inflammatory agents, and so on).

In pharmaceutical dosage forms, the compounds may be administered in the form of their pharmaceutically acceptable salts. The following methods and excipients are given by way of example only and are not in any way limiting. For preparations for oral administration, our compositions can be used alone or in combination with suitable additives for the manufacture of tablets, powders, granules or capsules, for example, with conventional additives such as lactose, mannitol, corn starch or potato starch; with binding agents such as crystalline cellulose, cellulose derivatives, gum arabic, corn starch or gelatins; with disintegrants such as corn starch, potato starch or sodium carboxymethyl cellulose; with lubricants, such as talc or magnesium stearate; and, if desired, with diluents, buffering agents, wetting agents, preservatives and flavoring agents. PFC should be included in the composition for injection by dissolving, suspending or emulsifying them in an aqueous or non-aqueous solvent such as vegetable or other similar oils synthetic aliphatic acid glycerides, esters of higher aliphatic acids or propylene glycol; and, if desired, with conventional additives such as solubilizers, isotonic agents, suspending agents, emulsifiers, stabilizers and preservatives.

PFCs can be used in an aerosol composition for inhalation administration. The compounds of the present invention can be incorporated into suitable pressure propellants such as dichlorodifluoromethane, propane, nitrogen and the like. In addition, PFCs can be incorporated into suppositories by mixing with a variety of bases, such as emulsifying bases or water-soluble bases. The compounds of the present invention can be administered rectally using a suppository.

A suppository may contain excipients, such as cocoa butter, carboax, and polyethylene glycols, which melt at body temperature but are solid at room temperature. Standard dosage forms for oral or rectal administration, such as syrups, elixirs and suspensions, where each unit dose, for example, a teaspoon, tablespoon, tablet or suppository, can contain a predetermined amount of a composition containing one or more components of the composition of the present invention.

Similarly, unit dosage forms for injection or intravenous administration may contain mixtures of the components of the present invention in a composition in the form of a solution in sterile water, normal saline, or another pharmaceutically acceptable carrier. Implants for sustained release of compositions are well known in this type scientific technique. Implants are made in the form of microspheres, plates, and possible other options, with biodegradable or non-biodegradable polymers.

For example, lactic and/or glycolic acid polymers form a degradable polymer that is well tolerated by the host. An implant containing the PFC according to the invention is positioned close to the focus of the pathology, so that the local concentration of the active agent is increased compared to other areas of the body. As used herein, the term "unit dosage form" refers to physically discrete units suitable for use as single doses for human and animal subjects. Each unit containing a predetermined amount of compounds of the present invention, which, according to calculations, is sufficient to provide the desired effect, together with a pharmaceutically acceptable diluent, carrier or excipient.

The descriptions of the unit dosage forms of the present invention depend on the particular mixture used, the effect to be achieved, and the pharmacodynamics of the mixture used in the host. Pharmaceutically acceptable excipients, such as excipients, adjuvants, carriers or diluents, are generally available. In addition, pharmaceutically acceptable excipients are generally available, such as pH adjusting agents and buffering agents, tonicity agents, stabilizers, wetting agents and the like. Typical doses for systemic administration range from 0.1 pg to 1000 milligrams per kg of subject body weight per administration. A typical dose may be one tablet for administration from two to six times a day, or one capsule or sustained-release tablet for administration once a day with a proportionally higher content of the active ingredient.

The effect of prolonged release may be due to the materials of which the capsule is made, which dissolve at different pH values, capsules that provide a slow release under the influence of osmotic pressure or by any other known controlled release method, including based on covalent modification of bacterial spores. Those skilled in the art will appreciate that dose levels may vary depending on the particular structure or mixture, the severity of the symptoms, and the subject's predisposition to side effects. Some of the specific structures and compositions are more potent than others. Preferred doses of this composition can be readily determined by those skilled in the art in a variety of ways.

The preferred method is to measure the physiological activity of PFC. One of the methods of interest is the use of liposomes as a vehicle for delivery. Liposomes fuse with the cells of the target region and ensure the delivery of liposome contents into the cells. The contact of the liposomes with the cells is maintained for a time sufficient for fusion using various methods of maintaining contact, such as isolation, binding agents and the like.

In one aspect of the invention, liposomes are designed to produce an aerosol for pulmonary administration. Liposomes can be made with purified proteins or peptides that mediate membrane fusion, such as Sendai virus or influenza virus and so on. Lipids can be in any useful combination of known liposome forming lipids, including cationic or zwitterionic lipids, such as phosphatidylcholine.

The remaining lipids will usually be neutral or acidic lipids, such as cholesterol, phosphatidylserine, phosphatidylglycerol and the like. To obtain liposomes, the method described by Kato et al. (1991) J. Biol. Chem. 266: 3361 is utilized. Generally speaking, lipids and a composition for incorporation into liposomes containing peptides are mixed in a suitable aqueous medium, in a suitably salty medium, where the total solids content will be in the range of about 110 wt. %. After vigorous stirring for short periods of approximately 5-60 seconds, the tube is placed in a warm water bath at approximately 25-40° C. and this cycle is repeated approximately 5-10 times. The composition is then sonicated for a suitable period of time, typically approximately 1-10 seconds, and optionally further mixed with a vortex mixer. Then the volume is increased by adding an aqueous medium, usually increasing the volume by about 1-2 times, followed by shaking and cooling. The method allows to include supramolecular structures with high total molecular weight, such as modified microbial spores, in liposomes.

Compositions with Other Active Agents

For use in the methods under consideration, the PFCs of the invention can be formulated with other pharmaceutically active agents, in particular other antimicrobial and antiviral agents. Other agents of interest also include a wide range of antianginal, antihypertensive, thrombolytic, anti-inflammatory agents known in the art. Classes of drugs for the treatment of viral and microbial diarrhea, influenza and its complications are presented in standardized treatment protocols for this pathology and can be combined with patented PFC. Cytokines, such as interferon gamma, tumor necrosis factor alpha, interleukin 12, and so on, may also be included in the PFC composition of the invention. The present invention is further described by the following examples, which should not be construed as limiting the scope of the invention.

Example 4. Protective Antiviral Activity of the Composition Obtained in Example 2, for Example, the Prevention of Mortality in Mice Infected with the H1N1 Influenza Virus (California 2011)

Tests were carried out on 10 groups of young white laboratory mice, 10 in each group. To create immunodeficiency, all animals were injected intraperitoneally with cyclophosphamide once at a dose of 100 mg/kg 2 times a week: in group A, animals were orally given 0.2 ml of water instead of the CMSB composition daily 1 time per day for 10 days. This group acted as a positive control. The second group was administered KCMSB (option with *S. boulardii*) at a dose of 0.2 ml per animal orally. The third to sixth groups introduced different variants of the KCMSB. The seventh group was administered Lactovit forte (BK with vitamins), the eighth group was administered Enterol (*S. boulardii*), the ninth group took KCMSB without *S. boulardii*, without benzyl isoquinolines and without germination activators (gibberellin and others). The tenth group orally received the standard antiviral drug remantadine at a dose of 75 mg/kg daily 1 time per day. After a week of taking cyclophosphamide, the animals developed immunodeficiency at the cellular link. After that, all animals were infected by inoculation of the H1N1 influenza virus (California 2011) at a dose of 10 ED90/mouse intranasally in 0.1 ml. The main criterion for the effectiveness of an anti-influenza drug is the mortality rate of animals after inoculation of the virus. In control group No. 9, the mortality rate was 90%. The research results are presented in table 4.

TABLE 4

The results of a study of the preventive antiviral effect against the H1N1 influenza virus of various compositions based on KCMSB

| Group No. | The name and composition of different variants | The number of surviving animals after the experiment, n = 10 | Percentage of surviving animals after experiment, % |
|---|---|---|---|
| 1 | Control-Normal Saline | 1 | 10 |
| 2 | KCMSB (variant with *S. Boulardii* and poppy seed extract) | 10 | 100 |
| 3 | KCMSB (papaverine variant) | 10 | 100 |
| 4 | KCMSB (variant of poppy seed extract)) | 9 | 90 |
| 5 | KCMSB (Maca variant, *S. boulardii,* gibberellin, carnitine) | 9 | 90 |
| 6 | All components of KHMSB without *S. Boulardii* and without modified spores of *B. coagulans,* without probiotics, only plant extracts, papaverine and plant growth activators) | 3 | 30 |
| 7 | Lactovit Forte | 3 | 30 |
| 8 | Enterol | 3 | 30 |
| 9 | KCMSB (modified disputes only) | | |
| 10 | Rimantadine | 5 | 50 |

P < 0.01, the difference is significant for all groups 2-10 against the control of group 1

As can be seen from table 4, the most effective compositions were variants of the invention, containing in one case papaverine and in another papaverine and *S. boulardii*. In both cases, all infected animals survived. Close results with 90% survival were observed in groups of 4-5 different embodiments of the compositions. A composition that does not include probiotics (including modified spores) had a weak prophylactic anti-influenza activity (Group 6) and protected only 30% of the animals from death. At the same time, the pure spores of *S. boulardii* from the Lactovit-Forte preparation had significantly less prophylactic antiviral activity (only 30% of the animals survived). The same picture was observed when using Enterol containing *S. boulardii*. The anti-influenza drug Remantadin was able to protect only 50% of the animals. Thus, for the manifestation of the maximum preventive antiviral activity against the background of chemical immunodeficiency, it is necessary to use the composition of KCMSB with all components of the prescription. Without probiotic components, in particular modified BC spores, the composition loses antiviral prophylactic activity. The presence of *S. boulardii* in the composition also prevented the death of animals in general. The mechanisms of this prophylactic effect are still not clear.

Example 5. Protective Antiviral Activity of KCMSB Against Rotaviruses

Rotavirus infection is an infectious disease caused by rotaviruses. It is the most common cause of diarrhea in children. This disease is characterized by an acute onset, mild symptoms of gastroenteritis or enteritis, a frequent combination of intestinal and respiratory syndromes in the initial period of the disease. Rotavirus infection is often incorrectly called intestinal flu, although rotavirus has nothing to do with influenza viruses.

In the experiment, the rotavirus subserotype strain IMI B117 was used (Kharkov, Ukraine). This strain causes typical diarrhea in rats with loose stools, an increase in body temperature, a change in behavior (decreased mobility), a drop in appetite, and a deterioration in the appearance of hair (they become ruffled). To fix these characteristics, each rat was placed in a small cage, the bottom of which was covered with white paper. The degree of diarrhea was fixed by the degree of contamination of the paper (in points from 1 to 10). The time of onset of signs of viral diarrhea was also recorded. The first stage of the experiment was the creation of an immunodeficiency background to increase the percentage of animals with viral diarrhea. For this, each animal was injected twice a week with 100 mg/kg of cyclospamide intravenously. Such a dose is able to suppress the cellular component of immunity and block the initial antiviral response of the body. After this week, the animals were given different HCBS oral formulations once a week, once a day, at a dose of 0.5 ml (0.2 g dry composition). Each composition was given to one group of rats, in each group of rats there were 6 animals. There were 10 groups in total. Table 5 presents the distribution of groups and the results of a study of the prophylactic antidiarrheal effect caused by rotavirus B. Each animal was injected with 5 ED90 of the virus in a culture medium in milk (1:1) orally.

TABLE 5

The results of a study of the preventive antiviral effect against rotavirus B of different compositions based on KCMSB

| Group No. | The name and composition of the solution | The number of animals with diarrhea (8-10 points *), (%), n = 6 | The time that viral diarrhea lasted, days | % efficiency ** |
|---|---|---|---|---|
| 1. | Control is Normal Saline | 6 | 9 | — |
| 2. | Cycloferon | 5 (17) | 7 (22) | 30 |
| 3. | KCMSB (variant with *S. boulardii* and poppy seed extract) | 0 | 0 | 100 |
| 4. | KCMSB (papaverine variant) | 0 | 0 | 100 |
| 5. | KCMSB (variant of poppy seed extract)) | 0 | 0 | 100 |
| 6. | KCMSB (option poppy extract, *S. boulardii*, gibberellin, carnitine) | 0 | 0 | 100 |
| 7. | All KCMSB without *S. Boulardii* and without modified spores of *B. coagulans*, without probiotics, only plant extracts, papaverine and plant growth activators) | 5 (17) | 3 (67) | 75 |
| 8. | Lactovit Forte | 3 (50) | 5 (44) | 72 |
| 9. | Enterol | 3 (50) | 5 (44) | 72 |
| 10. | KCMSB (modified disputes only) | 3 (50) | 5 (44) | 72 |

* 1 point-single spots on paper in cells, 10 points-massive diarrhea with continuous contamination of the paper litter, as well as a set of clinical signs of viral diarrhea.
** percentage of efficiency-the arithmetic average of the sum of the percent of sick animals and the percentage of reduction in the duration of the disease in relation to the control.
$P < 0.01$, the difference is significant for all groups 2-10 against the control of group 1 (Chi-square method)

As can be seen from table 5, none of the animals that received KCMSB containing covalently modified spores of BC together with benzoquinoline alkaloids, with plant extracts and activators of germination of spores did not get sick with viral enteritis and did not show any signs of diarrhea or signs of viral infection. The KCMSB component without probiotics was less effective and accounted for 75% of efficiency, while Lactovit-Forte and Enterol preparations showed only 72% of effectiveness. The least effective was cycloferon (30%), administered orally at a dose of 30 mg/kg body weight every other day. Thus, there is a synergistic activity of all the components included in the composition. The exclusion from the composition of either covalently chemically modified spores of BC or other components of the composition leads to a loss of effectiveness. In addition, attention should be paid to the higher degree of protection of animals with KCMSB compositions against Lactovit-Forte pharmaceutical preparations (BC and vitamins B12, B9) and Enterol (*S. boulardii*).

Example 6. Protective Antiviral Activity of KCMSB Against Coronaviruses

Respiratory coronavirus is represented by strains OC38, OC43, and the cause of enteritis is most often strain 229 E. The name is explained by the presence of a special ring on the surface of the viral particle: peplomers in the form of club-shaped spike-like outgrowths resembling a corona are present on the lipid membrane or supercapsid. Coronavirus can provoke damage to: the respiratory system; gastrointestinal tract; nervous system. The primary reproduction in the mucous membrane of the nasopharynx and respiratory tract, as a result, there is a profuse runny nose, and in children—bronchitis and pneumonia. In most cases, people encounter diarrhea and enteritis caused by coronaviruses Alphacoronavirus 1 strain IMI K105 (Kharkov, Ukraine) was used in the experiment. This strain causes typical diarrhea in rats with loose stools, an increase in body temperature, a change in behavior (decreased mobility), a drop in appetite, and a deterioration in the appearance of hair (they become ruffled). To fix these characteristics, each rat was placed in a small cage, the bottom of which was covered with white paper. The degree of diarrhea was fixed by the degree of contamination of the paper (in points from 1 to 10). The time of onset of signs of viral diarrhea was also recorded. The first stage of the experiment was the creation of an immunodeficiency background to increase the percentage of animals with viral diarrhea. For this, each animal was injected twice a week with 100 mg/kg of cyclophosphamide intravenously. Such a dose is able to suppress the cellular component of immunity and block the initial antiviral response of the body. After this week, the animals were given different HCBS formulations orally once a week, at a dose of 0.5 ml (0.2 g dry composition). Each composition was given to one group of rats, in each group of rats there were 6 animals. There were 10 groups in total. Table 6 presents the distribution of groups and the results of a study of the prophylactic antidiarrheal effect caused by coronavirus. Each animal was administered 1 ED90 of the virus in a culture medium orally

TABLE 6

Results of preventive antiviral action study for coronaviruses of different compositions based on KCMSB

| Group No. | The name and composition of the components | The number of animals with diarrhea (8-10 points *), (%), n = 6 | The time that viral diarrhea lasted, days | % efficiency ** |
|---|---|---|---|---|
| 1. | Control is physical. Solution | 6 | 9 | — |
| 2. | Cycloferon | 5 (17) | 7 (22) | 30 |
| 3. | KCMSB (version with *S. Boulardii* and poppy seed extract) | 0 | 0 | 100 |
| 4. | KCMSB (papaverine variant) | 0 | 0 | 100 |
| 5. | KCMSB (variant of poppy seed extract)) | 0 | 0 | 100 |
| 6. | KCMSB (variant of poppy, *S. boulardii,* gibberellin, carnitine) | 0 | 0 | 100 |
| 7. | All KCMSB components without *S. Boulardii* and without modified spores of *B. coagulans,* without probiotics, only plant extracts, papaverine and plant growth activators) | 4 (33) | 4 (55) | 71 |
| 8. | Lactovit Forte | 2 (67) | 5 (44) | 55 |
| 9. | Enterol | 2 (67) | 5 (44) | 55 |
| 10. | KCMSB (modified disputes only) | 2 (67) | 5 (44) | 55 |

* 1 point-single spots on paper in cells. 10 points-massive diarrhea with continuous contamination of the paper litter, as well as a set of clinical signs of viral diarrhea.
** percentage of efficiency-the arithmetic average of the sum of the percent of sick animals and the percentage of reduction in the duration of the disease in relation to the control.
$P < 0.01$, the difference is significant for all groups 2-10 against the control of group 1 (Chi-square method)

As can be seen from table 6, none of the animals that received KCMSB containing covalently modified spores of BC together with benzoquinoline alkaloids, plant extracts and activators of germination of spores did not get sick with viral enteritis caused by coronavirus, and did not show any signs of diarrhea or viral infection. The KCMSB component without probiotics was less effective and accounted for 75% of efficiency, while Lactovit-Forte and Enterol preparations showed only 71% of effectiveness. The least effective was cycloferon (30%), administered orally at a dose of 30 mg/kg body weight every other day. Thus, there is a synergistic activity of all the components included in the composition. The exclusion from the composition of either covalently chemically modified spores of BC or other components of the composition leads to a significant decrease in the effectiveness of prophylaxis. In addition, attention should be paid to the higher degree of protection of animals with KCMSB compositions against Lactovit-Forte pharmaceutical preparations (BC and vitamins B12, B9) and Enterol (*S. Boulardii*).

Example 7. Immunomodulatory Activity of KCMSB in Comparison with the Drug Lactovit-Forte To determine the effect of KCMSB preparations on the immunity of mice, animals were grouped according to the scheme described in example 3, except for the group with remantadine. There were 9 groups in total. Cyclophosphamide (CFA) was administered to all animals once at a dose of 250 mg/kg to induce immunodeficiency as shown in Example 3. After a week, they began to give samples of KCMSB orally at a dose of 0.2 ml (the dose contained 0.1 dry composition KCMSB).

Hsp70, NO, and Cytokine Synthesis Assay.

Isolation of murine peritoneal macrophages and spleen T-lymphocytes, measurement of TNF production was performed by enzyme-linked immunosorbent assay (ELISA) using the ELISA Kit (Mouse TNF-a ELISA Kit, PharMingen, BD Biosciences, San Jose, Calif., USA). NO Macrophages, 106 cells/ml, pH indicator with methylene red at 37° C. in a humidified atmosphere containing 5% CO2. The medium was enriched with 25 mM HEPES, 3% fetal bovine serum. Supernatants were collected after 21 hours and analyzed for N02. Griss reagent (containing 1% sulfanilamide/0.1% naphthylethylenediamine dihydrochloride and 2.5% H3PO4 (1:1)) used to evaluate N02, which served as an indicator of NO formation. After cultivation, 100 ml of each sample was placed in a 96-well plate with 100 ml of Griss reagent. Ten minutes later, the optical density was measured on a tablet spectrophotometer (Stat Fax 303 plus, Awareness technology inc., USA) at 590 nm.

Determination of the Ability of Lymphocytes to Express IL-2

Spleen lymphocytes, 1.5×106 cells/ml, were cultured for 72 hours in 24-well plates in 199 medium at 37° C. in a humidified atmosphere containing 5% CO2. The medium was supplemented with 25 mM HEPES, 5% fetal bovine serum and 5 mg/ml phytohemagglutinin (PHA). The concentration of IL-2 in the supernatant of cells stimulated PHA was measured by ELISA using polyclonal antibodies from rabbits against mouse IL-2 (BioRad, AbD Serotec, Raleigh, N.C., USA) and goat anti-rabbit IgG conjugated with Biotin (Agrisera Antibodies, Vannas, SWEDEN). After ABTS staining, the optical density was measured on a tablet spectrophotometer (Stat Fax 303 plus, Awareness technology inc., USA) at 405 nm. Statistical significance was calculated by t-student test in the modification of Bonferroni. Table 7 shows the results of the effects of KCMSB on mouse immunity.

TABLE 7

The effect of KCMSB in comparison with the drug Lactovit-Forte on the mice immunity.

| | Cells, tissues, lymphokines | | | | | | |
|---|---|---|---|---|---|---|---|
| | Il-2 products (ng/ml) | | | T | NO production in mouse | Number of macrophages | Number of |
| Groups | Splenic T lymphocytes | Blood plasma | Macrophages (TNF-a,) | cells (TNF-b) | macrophages µg/ml | (in millions) | splenocytes (million) |
| Control healthy mice | 76 ± 7 | 164 ± 10 | 16 ± 3 | 13 ± 2 | 10 ± 3 | 2.0 ± 0.1 | 126 ± 22 |
| Immunodeficiency Control after Cyclophosphamide | 12* ± 5* | 32* ± 10* | 3* ± 1* | 8* ± 2 | 6* ± 2* | 1.0* ± 0.1* | 87* ± 12* |
| KCMSB (option with *S. Boulardii* and poppy seed extract) | 87* ± 10* | 178* ± 12 | 19 ± 5 | 14 ± 2 | 12 ± 4 | 1.3 ± 0.2 | 133 ± 20 |
| KCMSB (option papaverine) | 85* ± 10* | 177* ± 12 | 18 ± 5 | 14 ± 2 | 13 ± 5 | 1.4 ± 0.3 | 135 ± 23 |
| KCMSB (variant of poppy seed extract)) | 89* ± 11* | 177* ± 14 | 19 ± 5 | 16 ± 3 | 12 ± 4 | 1.3 ± 0.2 | 129 ± 20 |
| KCMSB (variant of poppy, *S. boulardii*, gibberellin, carnitine) | 87* ± 10* | 179* ± 13 | 19 ± 5 | 16 ± 3 | 13 ± 5 | 1.4 ± 0.3 | 137 ± 23 |
| All components of KCMSB without *S. Boulardii* and without modified spores of *B. coagulans*, without probiotics, only plant extracts, papaverine and plant growth activators) | 50* ± 10 | 100* ± 10 | 7* ± 4* | 8 ± 2* | 10 ± 4 | 1.2 ± 0.1 | 106 ± 15 |

TABLE 7-continued

The effect of KCMSB in comparison with the drug Lactovit-Forte on the mice immunity.

| | Cells, tissues, lymphokines | | | | | | |
|---|---|---|---|---|---|---|---|
| | Il-2 products (ng/ml) | | | T | NO production in mouse | Number of macrophages | Number of |
| Groups | Splenic T lymphocytes | Blood plasma | Macrophages (TNF-a,) | cells (TNF-b) | macrophages μg/ml | (in millions) | splenocytes (million) |
| Lactovit Forte | 67* ± 9* | 100* ± 9 | 12 ± 2 | 10 ± 1 | 10 ± 1 | 1.0 ± 0.1 | 90 ± 10 |
| Enterol | 69* ± 9* | 98* ± 9 | 10 ± 2 | 9 ± 1 | 12 ± 1 | 1.2 ± 0.1 | 95 ± 12 |
| KCMSB (modified spores only) | 68* ± 8 | 100* ± 10 | 8 ± 4* | 9 ± 1* | 11 ± 1 | 1.1 ± 0.1 | 100 ± 14 |

*Statistically significantly different from both controls, P < 0.05.

As can be seen from table 7, the best result of the restoration of immunity to almost normal levels was observed in all experimental groups (3-6), where high-grade KCMSB compositions were used against the background of CFA—immunodeficiency. Moreover, the level of splenic T lymphocytes was statistically significantly higher than in the control. The only inexplicable indicator that goes beyond the concept of immunosuppression is the increase in IL-2 production by splenocytes above the control in group 5, where induced immunosuppression was observed. We connect this fact with uneven effect of CFA on different parts of the immune system and their non-synchronous stimulation by the spore form of *B. coagulans*. Unlike the composition of group 3, group 7 (without probiotics), although it stimulated immunity against control group 2, did not even restore it to the level of control group 1. Lactovit-Forte and Enterol restored immunity almost to the norm, similarly to chemically modified spores of CD. Higher indicators of the effect on the immunity of KCMSB compositions No. 3-5 are explained by the synergistic action of the components: stimulation germination of spores with gibberellin and other activators, stimulation of division of microbial cells and fungi by papaverine and/or poppy extract, effect on the immunity of plant extracts of licorice, *stevia* and *spirulina*.

The Main Advantages of Our Composition:

1. A powerful preventive effect against viral infections (influenza, coronavirus, rotavirus) comparable to the action of specific vaccines
2. Strong immunomodulatory effect
3. The rapid onset of the effect of activation of immunity after 8 hours (for unmodified spores of *Bacillus coagulans* 72 hours)
4. The possibility of introducing our composition into the composition of carbonated drinks, iced tea, ice cream, sweet foam in aerosol cans, creams, toothpastes, cosmetics. Modification of the surface of spores leads to an increase in their stability in the environment and to preservatives.
5. The ability to protect the product containing *Bacillus coagulans* spores from souring and spoilage for a long time, and the sour product will contain beneficial *Bacillus coagulans* bacteria that will not harm the body.
6. Products based on the proposed composition are able to stimulate the metabolism and energy of the body, which is very important in sports and during rehabilitation after serious illnesses, it can be useful in sports nutrition. This effect is caused by the synergism of spores and extracts: *spirulina, stevia*, alfalfa. For alfalfa, an anabolic effect and real benefits in sports training have been proven. These extracts are not included in the list of doping.

The invention claimed is:

1. A food, cosmetic or pharmaceutical composition comprising:
   a. a mixture of probiotics with an immunomodulating effect, comprising modified spores of the probiotic bacterium *B. coagulans*, the surface of which is covalently chemically modified by acylation with dicarboxylic and polycarboxylic acid anhydrides or halides to a degree of up to 15% by weight of the spores;
   b. papaverine or a raw material containing papaverine;
   c. plant extracts comprising glycosides, amino acids, and vitamins; and
   d. at least two components selected from gibberellin, para-aminobenzoic acid, carnitine, and an auxin.

2. The composition according to claim 1, further comprising probiotic fungus *S. boulardii* in an amount of from 1 to 10 lg CFU/ml per dose of the composition.

3. The composition according to claim 1, wherein the plant extracts with glycosides includes a licorice extract in an amount of from 0.05% to 0.5% by weight of the composition.

4. The composition according to claim 1, wherein the plant extracts with glycosides includes a *Stevia* extract in an amount of from 0.05% to 0.5% by weight of the composition.

5. The composition according to claim 1, wherein the plant extracts with glycosides includes a *spirulina* extract in an amount of from 0.05% to 5% by weight of the composition.

6. The composition according to claim 1, wherein the plant extracts with glycosides includes an alfalfa extract in an amount of from 0.05% to 5% by weight of the composition.

7. The composition according to claim 1, wherein the vitamins include cyanocobalamin.

8. The composition according to claim 1, wherein the vitamins include riboflavin.

9. The composition according to claim 1, wherein the vitamins include thiamine.

10. The composition according to claim 1, wherein the vitamins include folic acid.

11. The composition according to claim 1, wherein the plant extracts further comprise rutin.

12. The composition according to claim 1, wherein the vitamins include a mixture of cyanocobalamin, riboflavin, thiamine, folic acid, and rutin.

13. The composition according to claim 1, wherein the amino acids include arginine.

14. The composition according to claim 1, wherein the amino acids include taurine.

15. The composition according to claim 1, wherein the amino acids include lysine.

16. The composition according to claim 1, wherein the amino acids include a mixture of arginine, taurine and lysine.

17. The composition according to claim 1, wherein the modified spores of the probiotic bacterium *B. coagulans* are present in an amount of from 1 to 10 lg CFU/ml per dose of the composition.

18. The composition according to claim 1, wherein the raw material containing papaverine includes crushed ripe poppy seeds.

19. The composition according to claim 1, wherein the raw material containing papaverine includes an extract of mature poppy seeds.

20. The composition according to claim 1, wherein the compounds of the benzylisoquinoline group include papaverine.

21. The composition according to claim 1, comprising gibberellin in an amount of 0.01-0.05% by weight of the composition.

22. The composition according to claim 1, comprising para-aminobenzoic acid in an amount of 0.01-0.5% by weight of the product.

23. The composition according to claim 1, comprising carnitine in an amount of 0.1-1.0% by weight of the composition.

24. The composition according to claim 1, comprising the auxin in an amount of 0.01-0.05% by weight of the composition.

* * * * *